United States Patent
Gupta et al.

(10) Patent No.: US 11,020,014 B2
(45) Date of Patent: Jun. 1, 2021

(54) PHOTOPLETHYSMOGRAM DEVICE WITH SKIN TEMPERATURE REGULATOR

(71) Applicant: Microsoft Technology Licensing, LLC, Redmond, WA (US)

(72) Inventors: Sidhant Gupta, Seattle, WA (US); Jonathan Bernard Lester, Bellevue, WA (US); Jeremiah Wander, Seattle, WA (US); Jessica De Souza, Santo Amaro da Imperatriz (BR)

(73) Assignee: Microsoft Technology Licensing, LLC, Redmond, WA (US)

(*) Notice: Subject to any disclaimer, the term of this patent is extended or adjusted under 35 U.S.C. 154(b) by 162 days.

(21) Appl. No.: 16/206,708

(22) Filed: Nov. 30, 2018

(65) Prior Publication Data

US 2020/0170521 A1    Jun. 4, 2020

(51) Int. Cl.
*A61B 5/024*    (2006.01)
*A61B 5/0205*    (2006.01)
(Continued)

(52) U.S. Cl.
CPC ...... *A61B 5/02427* (2013.01); *A61B 5/02055* (2013.01); *A61B 5/1455* (2013.01); *A61B 5/7235* (2013.01); *A61F 7/08* (2013.01)

(58) Field of Classification Search
CPC .............. A61B 5/1455; A61B 5/14532; A61B 5/14552; A61B 5/6801; A61B 5/681; A61B 5/1491
See application file for complete search history.

(56) References Cited

U.S. PATENT DOCUMENTS 6,356,774 B1    3/2002    Bernstein et al.
6,633,771 B1 *    10/2003    Braig ................. A61B 5/14532
                                                                                600/310

(Continued)

FOREIGN PATENT DOCUMENTS

EP            1223851 A1    7/2002
WO       2016191307 A1    12/2016

OTHER PUBLICATIONS

"International Search Report and Written Opinion Issued in PCT Application No. PCT/US19/062889", dated: Mar. 13, 2020, 10 Pages.

(Continued)

*Primary Examiner* — Eric F Winakur
(74) *Attorney, Agent, or Firm* — Alleman Hall Creasman & Tuttle LLP

(57) ABSTRACT

A photoplethysmogram device is provided comprising a light source configured to emit light to illuminate skin, a photo-detector configured to receive the light illuminating the skin and generate an electrical output as a function of an intensity of the received light, a skin temperature regulator configured to heat and/or cool a temperature of the skin adjacent to the photo-detector and light source to increase the signal-to-noise ratio (SNR) of the electrical output from the photo-detector, and a processor configured to generate, based on the electrical output, an output signal indicative of blood properties, including physiological parameters such as blood pressure, heart rate, stroke volume, cardiac output, total peripheral resistance, blood vessel elasticity, and arterial oxygen saturation.

20 Claims, 12 Drawing Sheets

(51) Int. Cl.
   *A61B 5/1455* (2006.01)
   *A61F 7/08* (2006.01)
   *A61B 5/00* (2006.01)

(56) References Cited

U.S. PATENT DOCUMENTS

| | | | | |
|---|---|---|---|---|
| 6,912,413 | B2 * | 6/2005 | Rantala | A61B 5/14551 |
| | | | | 600/322 |
| 7,162,288 | B2 * | 1/2007 | Nordstrom | A61B 5/14551 |
| | | | | 600/323 |
| 8,078,244 | B2 * | 12/2011 | Melman | A61B 5/14558 |
| | | | | 600/316 |
| 10,874,352 | B2 * | 12/2020 | Huiku | A61B 5/14552 |
| 2003/0023151 | A1 * | 1/2003 | Khalil | A61B 5/14532 |
| | | | | 600/309 |
| 2015/0087928 | A1 | 3/2015 | Podhajsky et al. | |
| 2018/0235532 | A1 | 8/2018 | Newberry | |
| 2018/0279891 | A1 | 10/2018 | Miao et al. | |
| 2020/0029874 | A1 * | 1/2020 | Tang | A61B 5/14552 |

OTHER PUBLICATIONS

Guyton, et al., "Vascular Distensibility and Functions of the Arterial and Venous Systems", In the Text Book of Medical Physiology, Eleventh Edition, Chapter 15, Aug. 2003, 4 Pages.

Jeong, et al., "Effects of Skin Surface Temperature on Photoplethysmograph", In the Journal of Healthcare Engineering, Volume , Issue 4, Dec. 2014, 11 Pages.

Njoum, et al., "Investigation of Finger Reflectance Photoplethysmography in Volunteers Undergoing a Local Sympathetic Stimulation", In Journal of Physics Conference Series, vol. 450, Issue 1, Jan. 2012, 7 Pages.

* cited by examiner

Type IV (olive, moderate brown skin)

Type II (white, fair skin)

CONTROL HEAT APPLIED TO SKIN

266% SNR improvement

Type IV (black, very dark brown to black skin)

PHOTOPLETHYSMOGRAM DEVICE WITH SKIN TEMPERATURE REGULATOR

BACKGROUND

Photoplethysmography (PPG) is a non-invasive optical sensing technique where light is used to illuminate a region of the body (often an earlobe, finger-tip, or the wrist), and changes in the reflected or transmitted light intensity as a result of absorption by bodily fluids, typically blood, are used to sense physiological parameters such as blood pressure, heart rate, stroke volume, cardiac output, total peripheral resistance, blood vessel elasticity, and arterial oxygen saturation. PPG technology has been adopted widely in clinical settings, in in-home healthcare products, and has been incorporated into the heart-rate sensing systems found on modern fitness watches, for example.

SUMMARY

A photoplethysmogram device is provided comprising a light source, a photo-detector, a skin temperature regulator, and a processor. The light source is configured to emit light to illuminate skin. The photo-detector is configured to receive the light illuminating the skin and generate an electrical output as a function of an intensity of the received light. The skin temperature regulator is configured to regulate a temperature of the skin, the skin temperature regulator being a heating and/or cooling mechanism configured to heat and/or cool the skin. The processor is configured to generate, based on the electrical output, an output signal indicative of blood properties.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Furthermore, the claimed subject matter is not limited to implementations that solve any or all disadvantages noted in any part of this disclosure.

DETAILED DESCRIPTION

PPG technology is often used to extract an arterial blood volume pulse waveform from the output signal of the PPG sensor. The extracted pulse waveform may then be used to determine the heart rate of the person wearing the PPG device. The pulse transit time (PTT), or the amount of time it takes for a pulse wave to travel through the user's arteries from one arterial site to another arterial site on the user's body, can also be determined from the pulse waveform to analyze as one indicator of blood pressure, arterial compliance, and the hardening of arterial walls.

In a PPG device, a photo-detector configured to receive the light illuminating the skin and generate an electrical output as a function of an intensity of the received light. The electrical output comprises an alternating current (AC) component and a direct current (DC) component. The AC component may reflect blood flow dynamics, while the DC component may reflect activities of the autonomic nervous system as well as skin tone, light absorption in the tissues, veins, and other physiological parameters. When placed on peripheral regions of the body, such as the wrist, finger, or the earlobe, the pulses measured by the PPG device may be similar to central pressure pulses in the aortic root and the ascending aorta. Accordingly, peripherally placed PPG devices may be used to evaluate the overall cardiovascular state of patients.

The amount of light passing through the skin is highly dependent on 1) the intensity/wavelength of the light, 2) the skin tone of the wearer, and 3) other parameters like device placement, underlying tissue heterogeneity, etc. PPG-based devices do not function equally on all wearers. Wearers with poor circulation or dark skin tone often require significant increases in power consumption for the devices to function due to increased light intensity requirements. As most of these devices are wearable and thus battery-operated, this poses a notable challenge. Even in cases where battery is not of concern, the intensity of light used can only be made bright to a certain level due to thermal management issues (i.e. too bright of a light can burn someone). The consequence is that device designers generally accept a low signal-to-noise ratio (SNR) for these individuals. Additionally, in colder environments the blood perfusion decreases as the vessels constrict. This also results in a poor SNR, making it difficult to extract desired physiological parameters from the optically-sensed signals.

Figure 1:
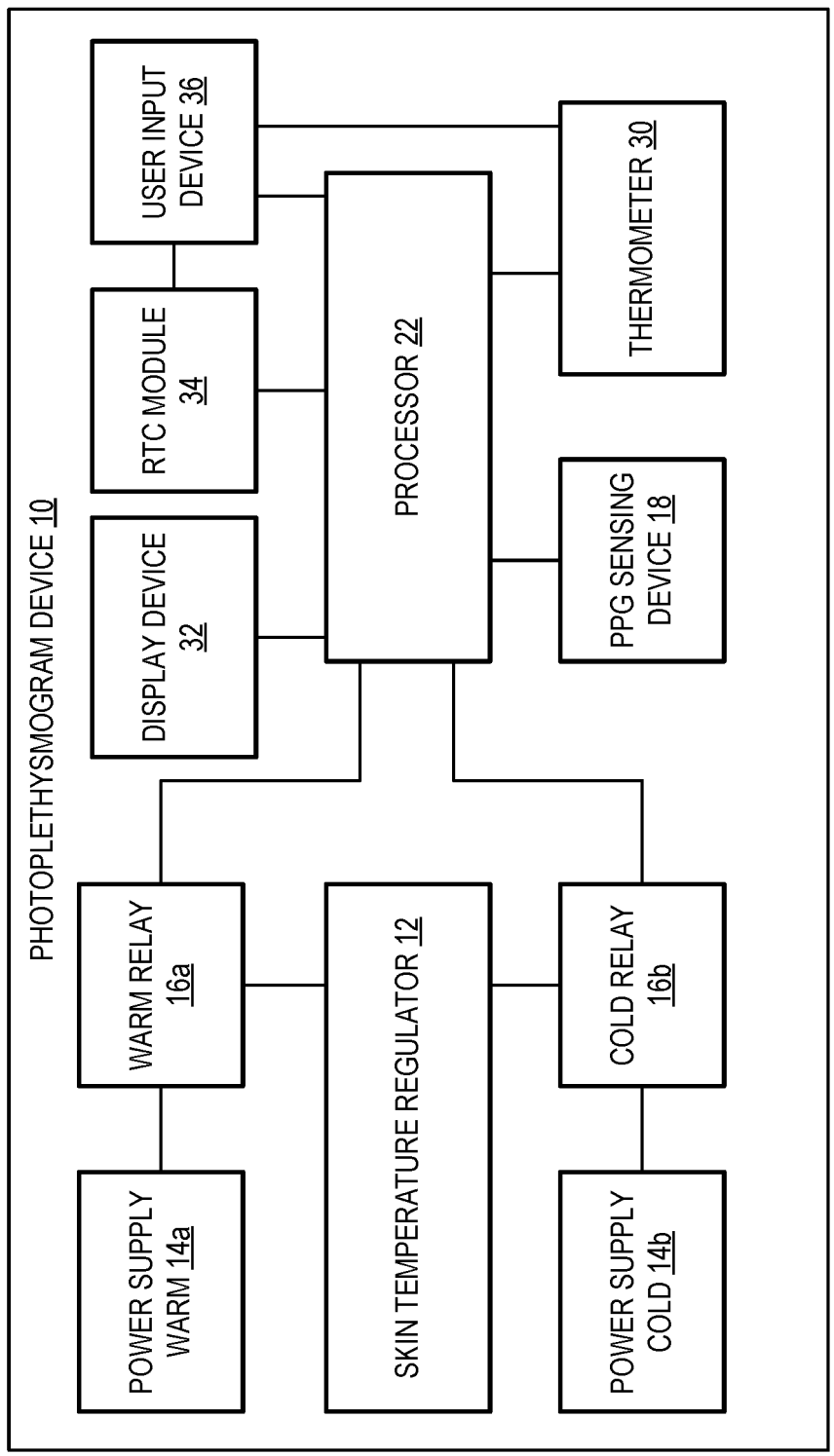
FIG. 1 illustrates a photoplethysmogram device according to one embodiment of the present disclosure.
Figure 2A:
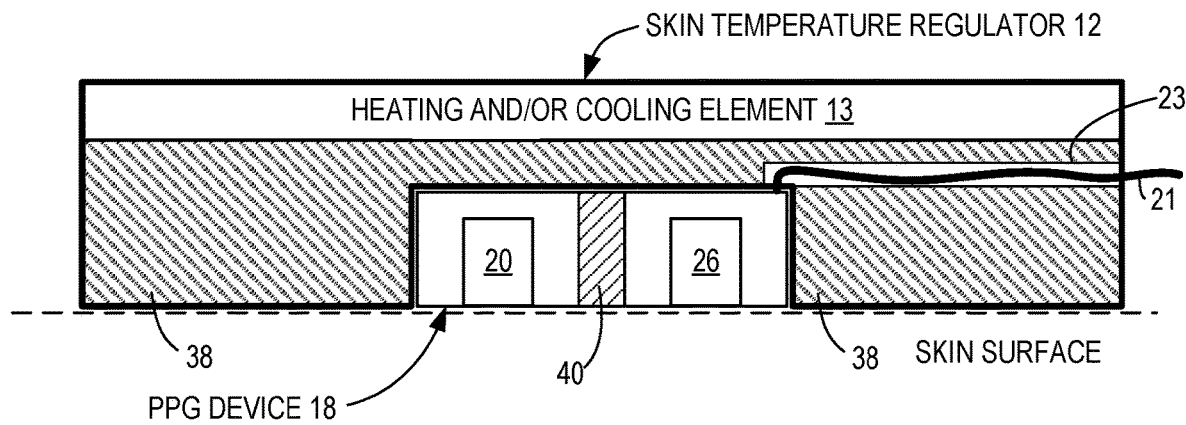
FIG. 2A illustrates a cross-sectional view of a photoplethysmogram device according to the embodiment of FIG. 1.
Figure 2B:
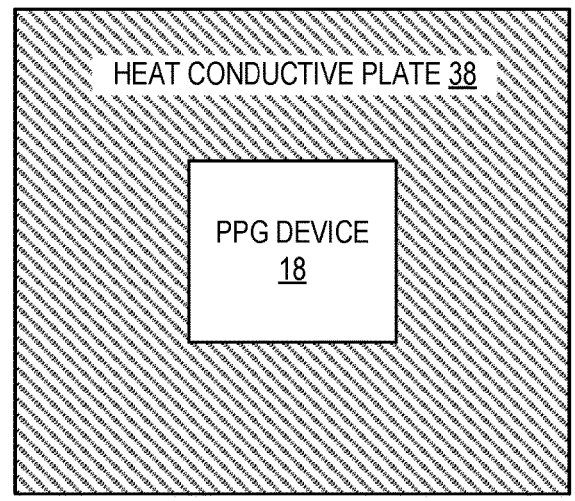
FIG. 2B illustrates a back, skin-facing surface of a photoplethysmogram device according to the embodiment of FIG. 1.

In view of the above described issues, referring to FIGS. 1, 2A, and 2B, a photoplethysmogram device 10 is provided comprising a light source 20 configured to emit light to illuminate skin, a photo-detector 26 configured to receive the light illuminating the skin and generate an electrical output as a function of an intensity of the received light, a skin temperature regulator 12 configured to regulate a temperature of the skin, the skin temperature regulator 12 being a heating and/or cooling mechanism configured to heat or cool the skin, and a processor 22 configured to generate, based on the electrical output, an output signal indicative of blood properties, including physiological parameters such as blood pressure, heart rate, stroke volume, cardiac output, total peripheral resistance, blood vessel elasticity, and arterial oxygen saturation. The skin temperature may be provided adjacent to the light source 20 and the photo-detector 26 to heat or cool the skin adjacent to the light source 20 and the photo-detector 26, which may be included in a PPG sensing device 18 coupled to the processor 22. The photoplethysmogram device 10 may be implemented in a wristband or other wearable form factors configured to wrap around a person's forearm, upper arm, torso, upper leg, lower leg, or ankle. The wristband may take the form of a wrist watch or a smart watch with its attendant computing, display, and communication capabilities.

A thermometer 30 may be coupled to the processor 22 and configured to measure a temperature of the skin. The thermometer 30 is preferably a thermocouple, but alternatively may be an infrared temperature sensor. A warm power relay 16*a* and a cold power relay 16*b* may be coupled to the skin temperature regulator 12. The processor 22 may be configured to control the warm power relay 16*a* and the cold power relay 16*b* to control the skin temperature regulator 12 to heat or cool the skin toward a predetermined skin temperature based on the measured skin temperature. In regulating the skin temperature, the processor 22 may further implement a feedback loop or a temperature control loop to control the skin temperature within a predetermined skin temperature range that includes the predetermined skin temperature. The predetermined skin temperature is set within a local heat tolerance range that varies by individual, which may be, for example, between 88° F. and 109° F.

For example, when the processor 22 controls the skin temperature regulator 12 to heat the skin, the processor 22 may control the warm power relay 16*a* to cause the warm power supply 14*a* coupled to the warm power relay 16*a* to supply power to the skin temperature regulator 12 to heat the skin, causing local vasodilation. When the processor 22 controls the skin temperature regulator 12 to cool the skin, the processor 22 may control the cold power relay 16*b* to cause the cold power supply 14*b* coupled to the cold power relay 16*b* to supply power to the skin temperature regulator 12 to cool the skin, causing local vasoconstriction. Additionally, the processor 22 may adjust the predetermined skin temperature, or the target skin temperature based on the tone of the skin, so that the intensity of the heating or cooling is greater at darker skin tones to compensate for the lower signal-to-noise ratio (SNR) values at darker tones. For example, the skin may be heated to warmer temperatures for darker skin tones than for lighter skin tones to achieve a similar target SNR. However, it will be appreciated that the adjustment of the target skin temperature may not be limited to being based on skin tone, and may be based on factors, such as the cardiovascular risk factors of the user including age, gender, family history, current medications, and personal medical history.

The processor 22 may be coupled to user interfaces, such as a display device 32 or a transceiver, to provide information about the blood properties generated by the processor 22 based on the electrical output generated by the photo-detector 26. For example, the transceiver (not pictured) may include a USB port for a wired communication or an RFID or Bluetooth wireless transceiver communicating to a user device or other type of remote device.

The processor 22 may further be coupled to a real time clock (RTC) module 34 which is configured to accurately keep track of time for the processor 22. Accordingly, the processor 22 may time the measurement of the skin relative to the timing of the heating and/or cooling of the skin. For example, the processor 22 may time the measurement of the skin to coincide with the heating or cooling of the skin, or time the measurement of the skin to be after the heating or cooling of the skin has completed, and the power relays 16*a*, 16*b* coupled to the skin temperature regulator 12 are turned off. It will be appreciated that the measurement of the skin includes the illumination of the skin by the light source 20, the reception of the light illuminating the skin by the photo-detector 26, and the generation of electrical output by the photo-detector 26 indicating a function of an intensity of the received light. Therefore, the processor 22 may be configured to generate the output signal indicative of blood properties after controlling the skin temperature regulator 12 to heat or cool the skin to the predetermined skin temperature.

The processor 22 may be further coupled to a user input device 36, which may be a push button or switch, which is configured to receive a user input to control the skin temperature regulator 12. For example, the user input device 36 may be configured to be a stop button that is pushed by a user when the user desires the heating or cooling operation of the skin temperature regulator 12 to stop.

The skin temperature regulator 12 includes a heating and/or cooling element 13, which may be a thermoelectric heat pump, an electric heater, or a heating element such as a heating plate. An example of a thermoelectric heat pump may be a Peltier cooler with two sides: a skin facing side and an outward facing side. The Peltier cooler is a refrigerant-free electric heater and cooler that can be electrically controlled to either heat or cool a surface. For example, the Peltier cooler may transfer heat from the skin facing side of the device to the outward facing side to cool the skin, or transfer heat from the outward facing side to the skin facing side to heat the skin. The heating element may be an induction heating apparatus.

As shown in FIGS. 2A and 2B, the skin temperature regulator 12 comprises a heating and/or cooling element 13 and a heat conductive plate 38, such as a metal plate manufactured of a material such as copper may be attached to the surface of the skin temperature regulator 12 to act as the thermal interface and buffer between the subject's skin and the heating and/or cooling element 13. It will be appreciated that other conductive metals or alloys besides copper may alternatively be substituted in the heat conductive plate 38 to act as a thermal buffer. As demonstrated in the cross-sectional view of FIG. 2A, the heat conductive plate 38 may also surround the PPG sensing device 18 to act as a buffer between the heating and/or cooling element 13 and the PPG sensing device 18. Within the PPG sensing device 18, a buffering member 40 may isolate the light source 20 from the photo-detector 26 to ensure that that photo-detector 26 only receives light illuminating the skin. A conduit 23 may be provided within the heat conductive plate 38 and/or the heating and/or cooling element 13 to pass wiring 21 between the PPG sensing device 38 and the processor 22. As demonstrated in the view of FIG. 2B illustrating the back, skin-facing surface of the photoplethysmogram device 10, the PPG sensing device 18 may be surrounded by the heat conductive plate 38 acting as a buffer between the skin and the heating and/or cooling element 13.

It will be appreciated that the skin temperature regulator 12 is not limited to Peltier coolers and electric heaters. For example, in alternative embodiments, the skin temperature regulator 12 may be a temperature gradient device utilizing heat generated by CPUs or state change compounds (expanding gases/chemical reactions). The skin temperature regulator 12 is not necessarily limited to the use of heat as an external stimulus, and alternatively may be a topical injection or application device injecting or applying compounds that cause local vasodilation in the skin.

Further, the skin temperature regulator 12 may not be limited to one heating and/or cooling element in the photoplethysmogram device 10, and multiple heating and/or cooling elements may alternatively be provided on the device to produce various gradient effects at one location on the skin. Measurement and actuation may occur at multiple points on the body with different actuation sources (heating, cooling, topical applications, intradermal injections, and combinations thereof, for example) to understand the dynamics of an individual's physiological state. For example, there may be interesting characteristics seen by driving two points to different perfusion states and observing how the body responds.

Prior to making a measurement with the PPG sensing device 18, the heating functionality of the device may be turned on to warm the skin directly beneath and around the PPG sensing device 18. In accordance with this configuration, skin surface temperature is changed through local gradual cooling or heating through the direct, superficial application of a thermal gradient, actively manipulating the local vasoactive state to increase local vasodilation and increase a SNR of the PPG signal, which increases the resolution of the signal to make it possible to extract desired physiological parameters for clinical decision making. Additionally, the processor 22 may regulate an intensity of the light emitted by the light source based on the tone of the skin, so that the intensity of the emitted light is greater at darker skin tones to compensate for the opacity of the skin at darker tones.

Higher resolution may allow the detection of subtle morphologic features in the PPG signal, thereby increasing the sensitivity of the PPG device to cardiac arrythmias such as atrial fibrillation, for example. By actively controlling vasodilation, the vascular system is driven to undergo physiological changes that improve optical signal quality (i.e. SNR), thereby enabling more frequent/easier testing of cardiovascular health.

The heating or cooling of the skin surface may not only affect the SNR of the PPG signal, but also affect the amount and kind of signal change at different wavelengths of illuminating light penetrating the skin at different skin depths. Accordingly, the light source 20 may be configured to emit light at a plurality of different wavelengths to measure various physiological metrics.

The heating or cooling of the skin surface may be controlled to be gradual before measuring blood properties. For example, the processor 22 may control the skin temperature regulator 12 to gently heat the skin a few minutes before taking the measurement to achieve a high-quality PPG signal with no perceptible change in temperature to the user. The heating or cooling may occur for a predetermined period of time, such as between 1-5 minutes, or more specifically between 1-3 minutes, and most specifically for about 2 minutes, or for another period of time. The heating or cooling process may be controlled to be slow enough that a user does not notice that a skin temperature change is happening. Following the heating or cooling, in some examples, the heating or cooling may be ceased for a second predetermined period of time, such as 1-5 minutes, or more specifically 1-3 minutes, or most specifically 2 minutes, or other period, during which period the heat/cooling effect persists and the attendant measurement improvements discussed herein can be achieved. These heating or cooling cycles may be repeated, as desired.

Figure 3:
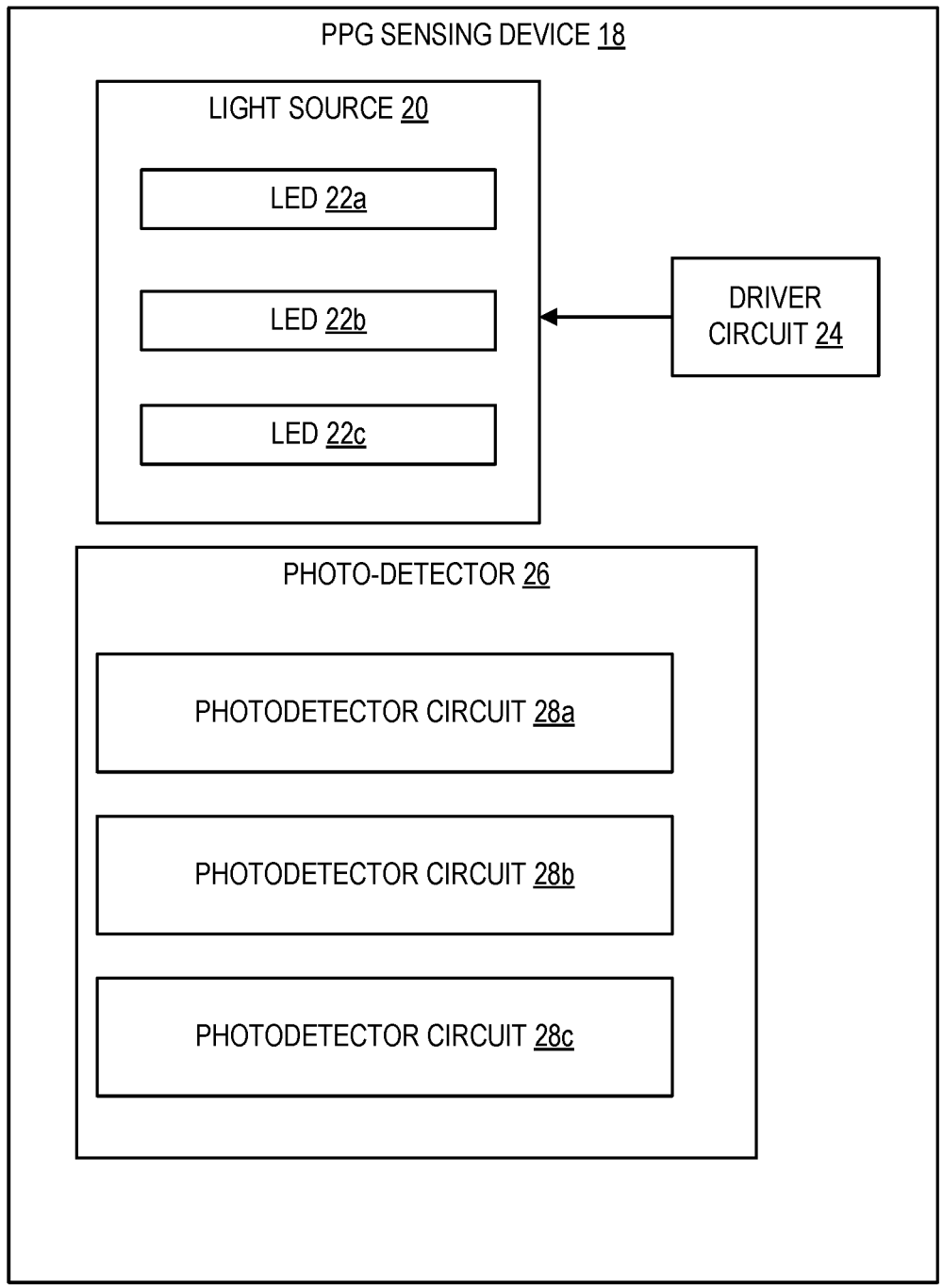
FIG. 3 illustrates a PPG sensing device according to the embodiment of FIG. 1.

As illustrated in a schematic block diagram in FIG. 3, the light source 20 and the photo-detector 26 may be packaged in a PPG sensing device 18 operatively coupled to the processor 22. The light source 20 may be one or a series of light emitting diodes (LED) 22a, 22b, and 22c configured to emit one or a plurality of wavelengths of light, including infrared (IR) light, ultraviolet (UV) light, near IR light or visible light, in response to the driver circuit. For example, the light source 20 may include a first LED 22a that emits visible light, a second LED 22b that emits infrared light, and a third LED 22c that emits UV light. The LEDs 22a, 22b, and 22c may be tunable to emit light over one or more frequencies or range of frequencies or spectrums in response to the driver circuit. The driver circuit 24 may be configured to control a power level, emission period, and frequency emission of the LEDs 22a, 22b, and 22c. The PPG sensing device 18 is thus configured to emit one or more wavelengths of light in one or more spectrums that is directed at the surface or epidermal layer of the skin tissue of a patient.

The photo-detector 26 of the PPG sensing device 18 may include one or more photo detector circuits 28a, 28b, and 28c. For example, a first photodetector circuit 28a may be configured to detect visible light of one wavelength, a second photodetector circuit 28b may be configured to detect visible light of another wavelength, and the third photodetector circuit 28c may be configured to detect IR light. Alternatively, the photodetectors may be configured to detect light across multiple spectrums and the signals obtained from the photodetectors added or averaged.

Figure 4:
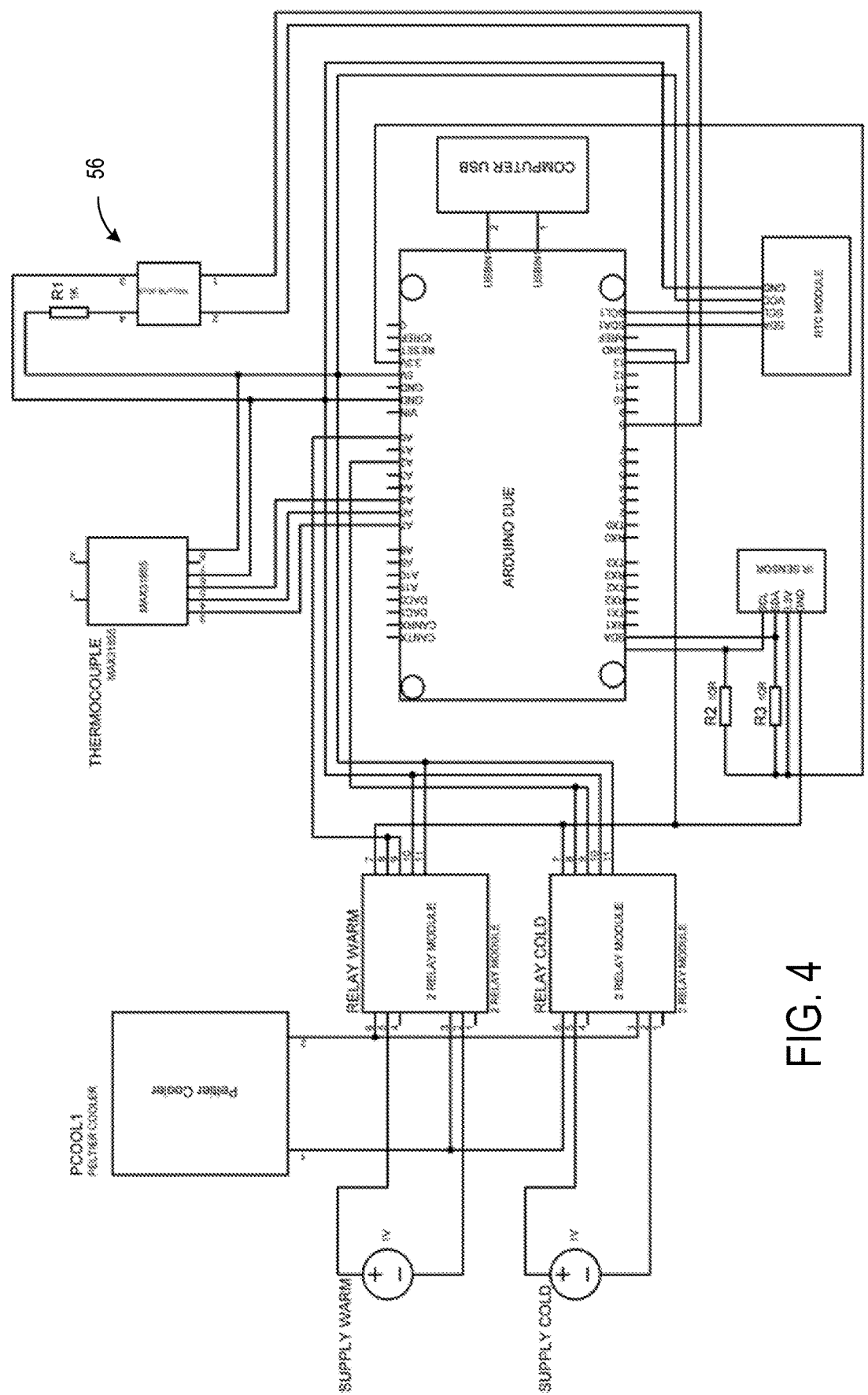
FIG. 4 shows a circuit diagram of a photoplethysmogram device which may be used in accordance with the embodiment of FIG. 1.

FIG. 4 illustrates a circuit diagram of the various components that comprise the photoplethysmography device of the embodiment of FIG. 1. It will be understood that the circuit diagram in FIG. 4 is merely depicted not to be limiting, but rather to be exemplary.

Figure 5:
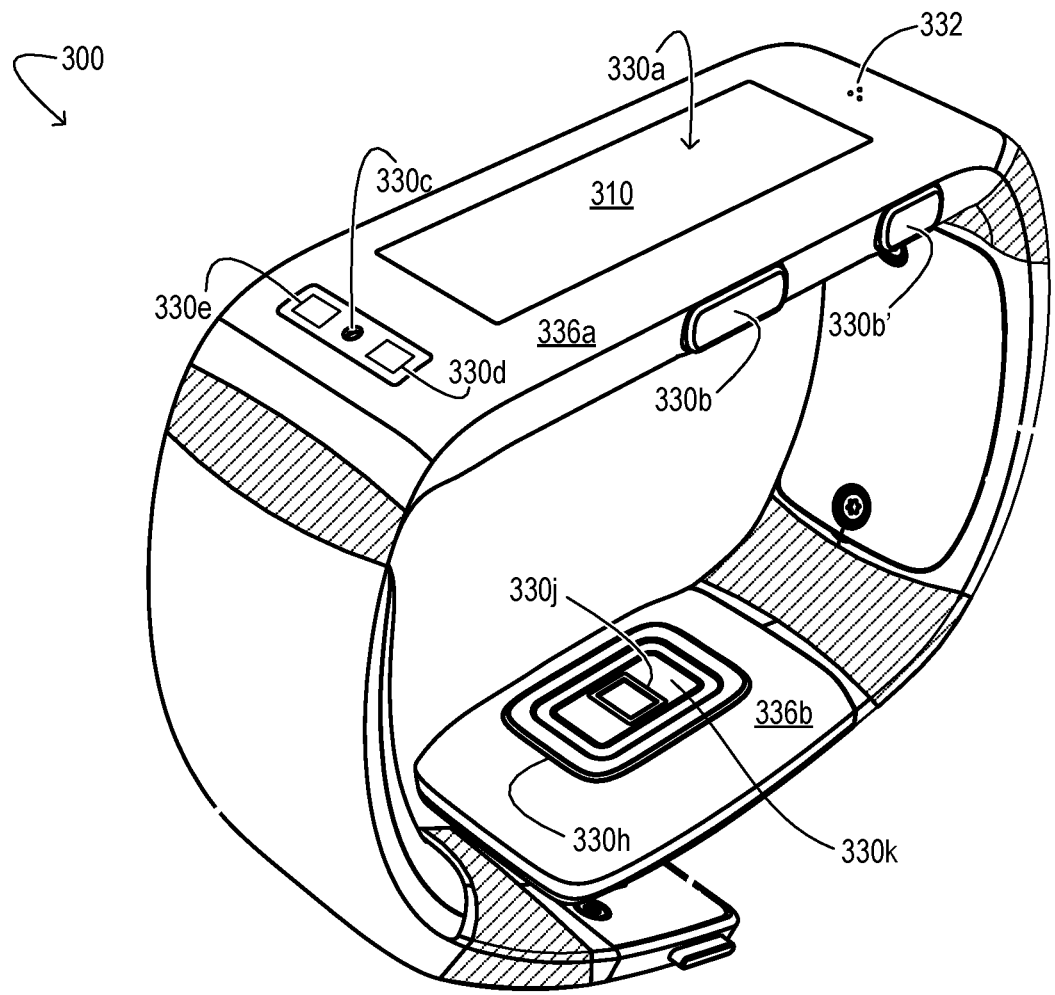
FIG. 5 shows aspects of a wearable computing device according to the embodiment of FIG. 1.

Referring to FIG. 5, one example of a wearable computing device 18 is given as a composite band 300. In composite band 300, touch-screen sensor 330a is coupled to display 310 and configured to receive touch input from the wearer. In general, the touch sensor may be resistive, capacitive, or optically based. Push-button sensors (e.g., microswitches) may be used to detect the state of push buttons 330b and 330b', which may include rockers. Input from the push-button sensors may be used to enact a home-key or on-off feature, control audio volume, microphone, etc.

Other sensors 330 of composite band 300 include microphone 330c, visible-light sensor 330d, and ultraviolet sensor 330e. The microphone provides input to compute system 322 that may be used to measure the ambient sound level or receive voice commands from the wearer. Input from the visible-light sensor, ultraviolet sensor, and ambient-temperature sensor may be used to assess aspects of the wearer's environment.

FIG. 5 shows a pair of contact sensors—charging contact sensor (not shown) arranged on display-carrier module 336a, and pillow contact sensor 330h arranged on pillow 336b. The contact sensors may include independent or cooperating sensor elements, to provide a plurality of sensory functions. For example, the contact sensors may provide an electrical resistance and/or capacitance sensory function responsive to the electrical resistance and/or capacitance of the wearer's skin. To this end, the two contact sensors may be configured as a galvanic skin-response sensor, for example. In the illustrated configuration, the separation between the two contact sensors provides a relatively long electrical path length, for more accurate measurement of skin resistance. In some examples, a contact sensor may also provide measurement of the wearer's skin temperature. In the illustrated configuration, a skin temperature sensor may be in the form a thermistor is integrated into charging contact sensor, which provides direct thermal conductive path to the skin. Output from ambient-temperature sensor and skin temperature sensor may be applied differentially to estimate of the heat flux from the wearer's body. This metric can be used to improve the accuracy of pedometer-based calorie counting, for example. In addition to the contact-based skin sensors described above, various types of non-contact skin sensors may also be included.

Arranged inside pillow contact sensor 330h in the illustrated configuration is an PPG sensor device 330j. The optical pulse-rate sensor 330j may include a light source and photo-detector to detect pulsating blood flow through the capillaries of the skin, and thereby provide a measurement of the wearer's blood properties, which may include at least one of blood pressure, heart rate, stroke volume, cardiac output, total peripheral resistance, blood vessel elasticity, and arterial oxygen saturation. Surrounding the PPG sensor device 330j is a skin temperature regulator 330k. In the illustrated configuration, optical pulse-rate sensor 330j and display 310 are arranged on opposite sides of the device as worn. The pulse-rate sensor alternatively could be positioned directly behind the display for ease of engineering.

To understand how the skin temperature regulator performs in increasing the SNR of the PPG signal for skin of different tones, the present inventors conducted measurements of the effects of heating skin of different tones on the SNR of the PPG signal. An experiment was performed, in which a participant wore a wrist device with surface skin temperature stimulation, PPG, EKG, motion, and temperature sensors. Five measurements were taken using this device, and five measurements taken on the opposite wrist using a similar device without temperature stimulation or measurement. In the former device, the skin temperature was changed randomly in the following order: normal to warm, warm to normal, normal to warm, and warm to normal, where normal is an unheated and uncooled skin temperature of around 91° F. and warm is a temperature of 105° F.

The experimental protocol was as follows. Height, weight, and skin tone data of the participant were collected. Each participant gave informed consent to participate in the experiment. Seated in a chair, a first custom wrist device was placed on the wrist of the non-dominant hand of the participant, and a second custom wrist device was placed on the wrist of the dominant hand of the participant. To ensure appropriate signal integrity, the wrist strap was tightened to a snug and comfortable fit. Electrocardiogram (ECG) electrodes were placed on the inner forearm of the participant for cardiac monitoring. The participant was informed that the stop button can be pressed if the skin temperature changes started to become uncomfortable. The PPG device was turned on, and after waiting approximately 30 seconds for the optical signal of the PPG device to stabilize, PPG data from the PPG device was collected for approximately 4 minutes at normal skin temperature (91° F.). After recording the normal skin temperature data, the skin temperature was increased or decreased using the wrist device until the target skin temperature had been reached. It typically took around 2 minutes for the skin temperature to increase or decrease to reach the target skin temperature. Once the target skin temperature was reached, PPG data from the PPG device was collected for approximately 4 minutes. After the collection of PPG data, the skin temperature was increased or decreased using the wrist device until the normal skin temperature (91° F.) was reached again. Once the normal skin temperature was reached, PPG data from the PPG device was collected for approximately 4 minutes.

Figure 6A:
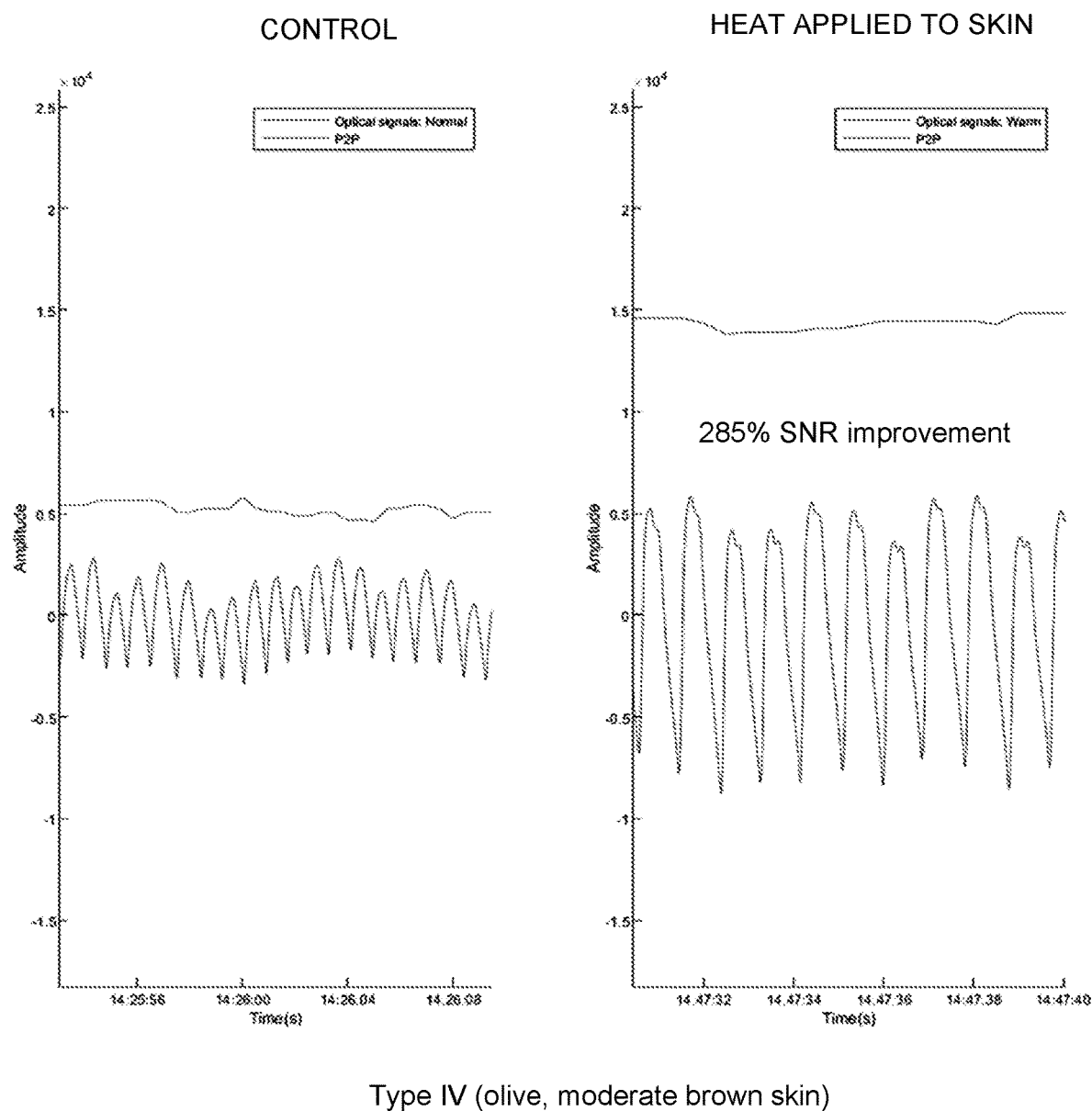
FIG. 6A-C plot the PPG signal for a skin temperature regulator of the embodiment of FIG. 1, which was applied to skin of different tones.
Figure 6B:
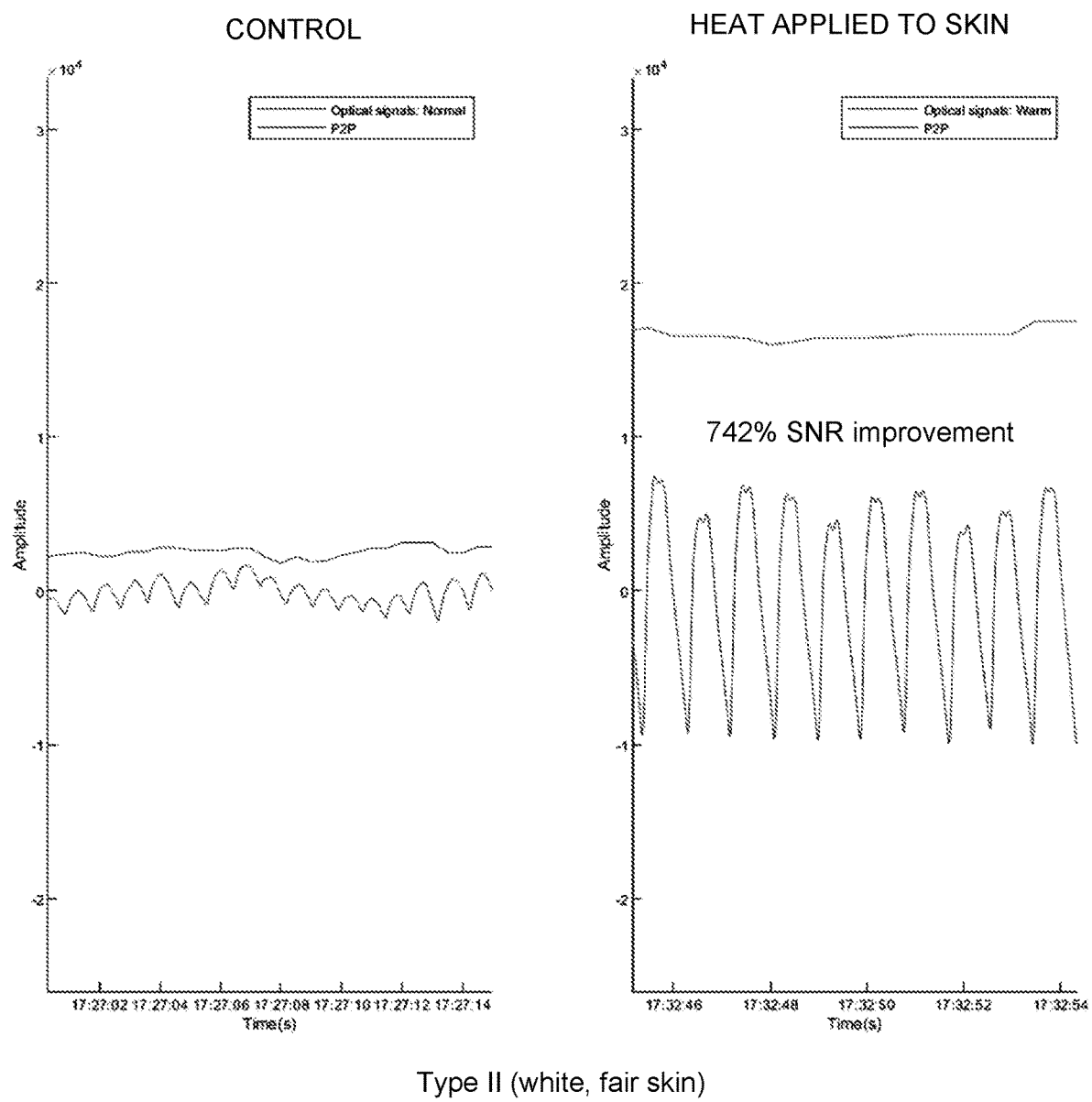
Figure 6C:
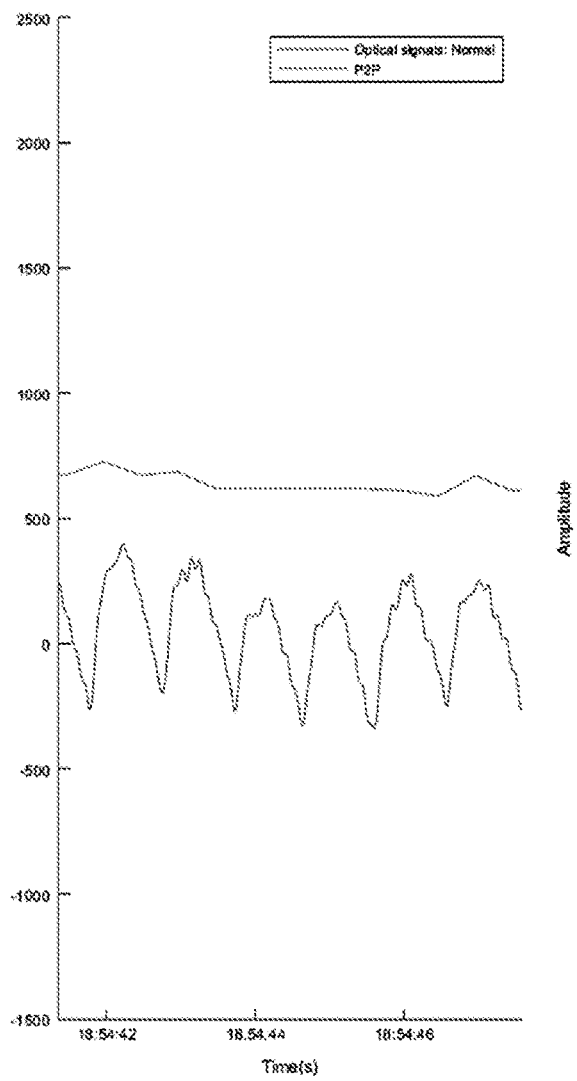
Figure 6C:
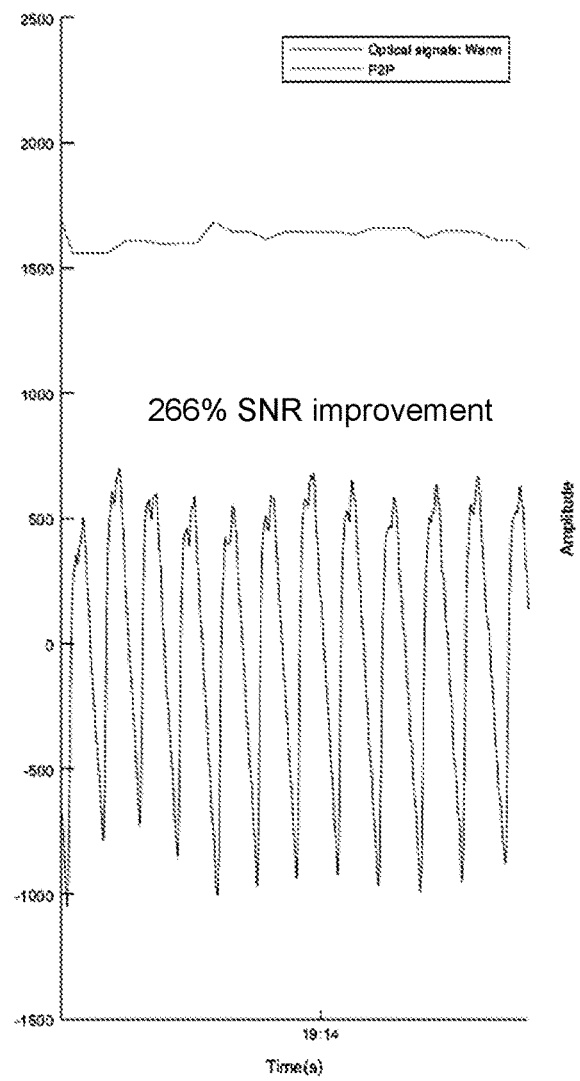

FIGS. 6A-C are plots demonstrating the change in signal quality and improvements as a function of heat application. FIG. 6A plots the PPG signal for a skin temperature regulator that was applied to skin classified Type IV, or olive, moderate brown skin, using the standardized Fitzpatrick scale. FIG. 6B plots the PPG signal for a skin temperature regulator that was applied to skin classified Type II, or white, fair skin. FIG. 6C plots the PPG signal for a skin temperature regulator that was applied to skin classified Type IV, or very dark brown to black skin.

As demonstrated in the results, for green light, 285% improvement in SNR was demonstrated for olive, moderately brown skin of type IV. For green light, 742% improvement in SNR was demonstrated for white, fair skin of type II. For green light, 266% improvement in SNR was demonstrated for black skin of type VI. Here, it will be appreciated that the effect on the SNR of the PPG signal was most pronounced for white skin. Nevertheless, improvements in SNR were demonstrated across all skin tones, and it has been demonstrated that by raising the skin temperature of the region surrounding the optical sensor, the quality of the PPG signal can be improved by as much as 300%.

Figure 6D:
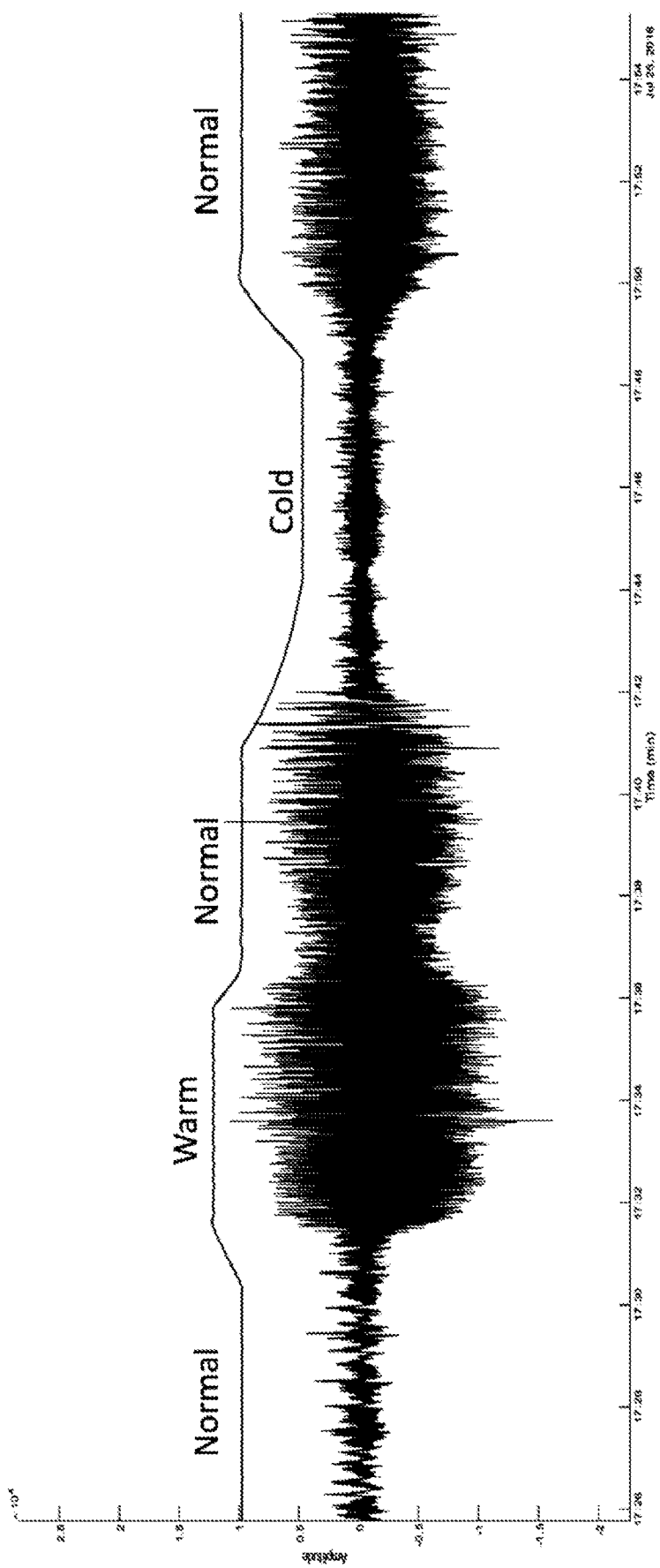
FIG. 6D plots the chronological changes in signal-to-noise ratio (SNR) of the PPG signal for a skin temperature regulator of the embodiment of FIG. 1, which was alternated between skin heating and cooling periods.

FIG. 6D plots the chronological changes in SNR of the PPG signal for a skin temperature regulator that was alternated between a heating period of heating the skin and a cooling period of cooling the skin. The responsiveness of the skin, or the changes in the electrical output of the photodetector in responding to sudden applications of heating and cooling can then be evaluated as a useful measure of cardiovascular health, especially for adjusting medications such as antihypertensives. As demonstrated in FIG. 6D, the increase in SNR resulting from the heating of the skin by the skin temperature regulator may persist even after the heating has stopped. Therefore, it will be appreciated that the processor may time the measurement of the skin to coincide with the heating of the skin by the skin temperature regulator, or time the measurement of the skin to be after the heating of the skin by the skin temperature regulator has stopped.

In accordance with the present invention, much better HR data (or pulse morphology if so desired) can be gathered on dark-skinned subjects. This is high impact because the traditional way to improve SNR in the industry has been to make the probing light/LED brighter. Applying an external stimulant induces additional blood perfusion in the top layers of the skin, thereby enabling clinical and fitness scenarios previously deemed difficult due to low SNR.

SNR can be increased to reduce the impact of noise artifacts that are generally present in and reduce the utility of PPG data. Respiratory and motion artifact are common examples of these waveform contaminants. When the SNR of the PPG signal improves, the morphology of the pulse signal changes in response to the stimulant, so that subtle morphologic details of the shape of the sensed pulse waveform can be studied in higher resolution, providing additional insight into the physiologic state of the wearer, which may be relevant to different clinical applications.

Figure 7:
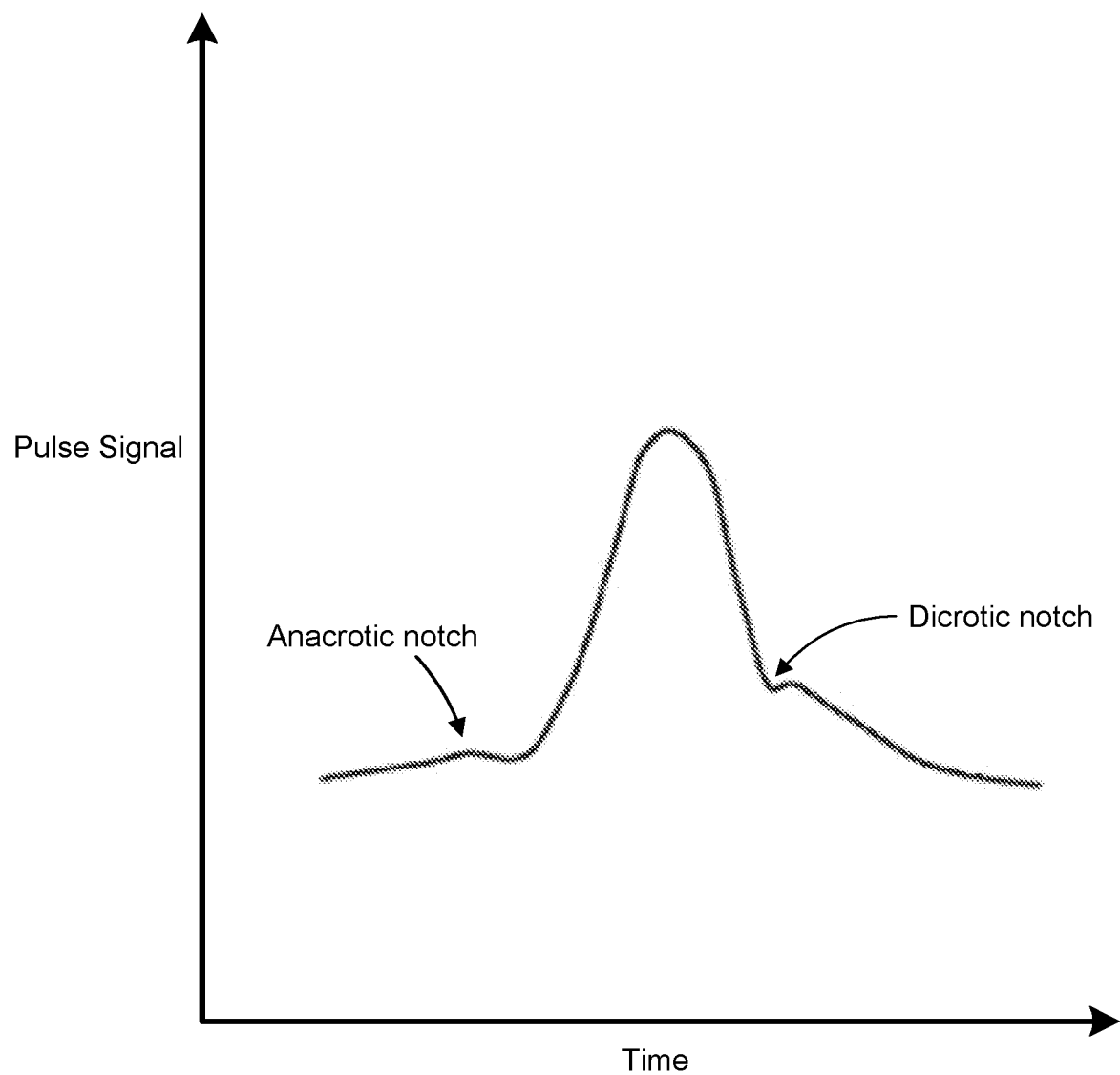
FIG. 7 illustrates an example blood volume pulse waveform featuring an anacrotic notch and a dicrotic notch that may be detected by the embodiment of FIG. 1.

Referring to the arterial pulse waveform depicted in FIG. 7, in some cases, the PPG signal contains a dicrotic notch in the waveform, which is typically a small, downward deflection or trough observed on the downstroke of an arterial pressure waveform that is believed to represent when the aortic valve closes. In some cases, the PPG signal contains an anacrotic notch in the waveform, which is typically a small inflection point that is observed during the initial upstroke or early downstroke of the waveform, and is generally considered to be the intersection of superimposed primary and reflected pulse waves in the arterial tree. The higher resolutions achieved by high SNR allow the identification of the diacritic notch and anacrotic notch in the arterial pulse waveform, which would otherwise not be possible at lower SNR. In clinical applications, the dicrotic notch is useful to identify in the arterial pulse waveform from the electrical output of the photo-detector as an indicator of aortic valve function, and also as the dividing line representing the end of the systolic phase and the beginning of the diastolic phase of cardiac contraction. When the arterial pulse waveform is measured in peripheral parts of the body, such as the wrist, the dicrotic notch is believed to represent the vascular resistance of the peripheral vessels.

This information could be utilized in clinical decision making as a useful measure of cardiovascular health. For example, clinical data about the responsiveness and recovery rate of a patient to the stimulus could inform a healthcare provider in adjusting medications such as antihypertensives. Patients could then forego invasive tests, such as conventional cardiac stress tests, to activate vasodilation. In serious cases, the abnormalities in the dicrotic notch may indicate that the aortic valve is failing to close normally, which may indicate stenosis or regurgitation. This information may be especially useful for high risk patients undergoing a preoperative evaluation who cannot perform conventional stress tests.

Figure 8:
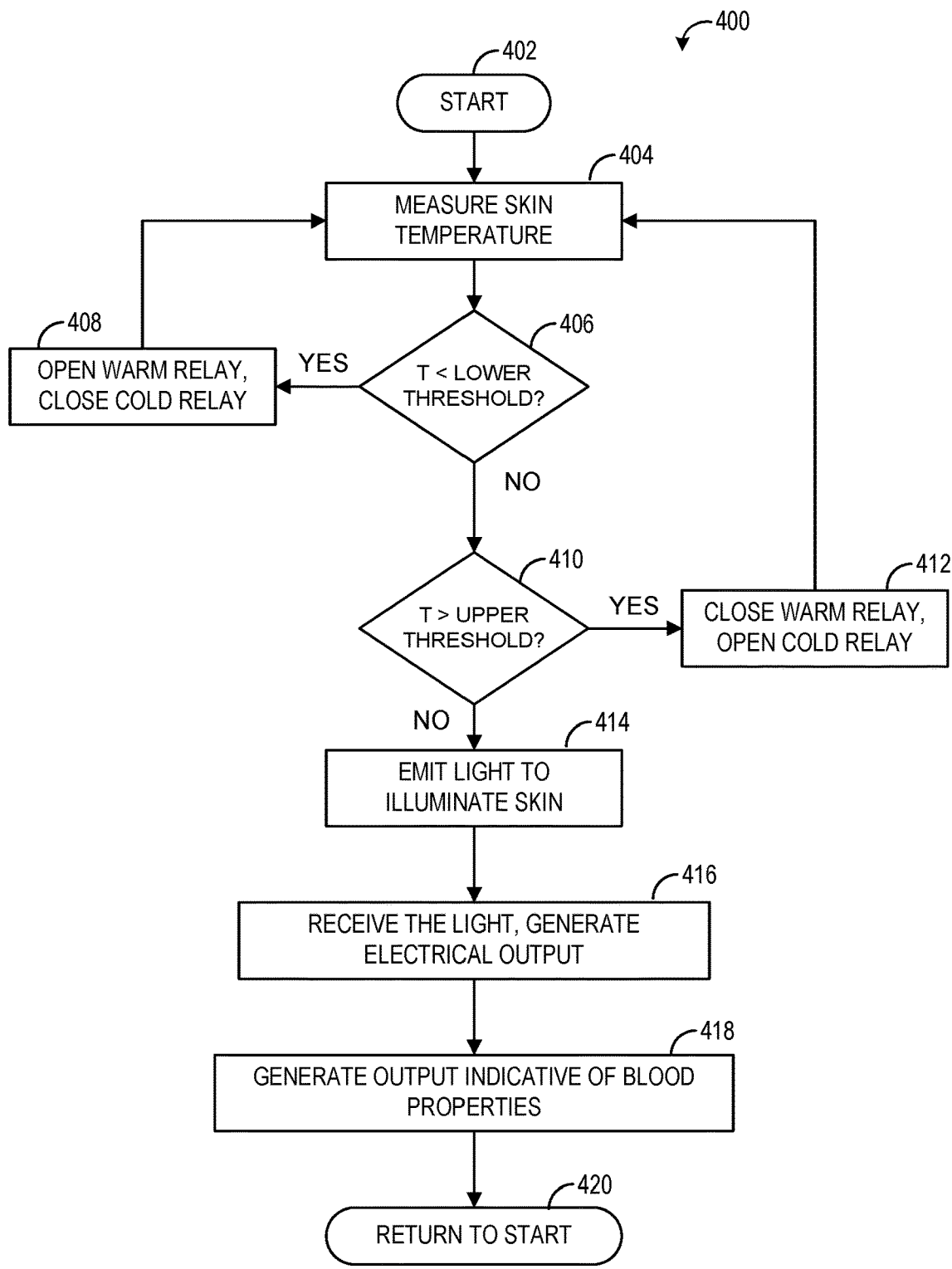
FIG. 8 shows an example photoplethysmography method according to one embodiment of the present disclosure.

FIG. 8 shows a flow diagram representing one photoplethysmography method 400 according to the embodiment of FIG. 1. The method 400 starts at 402. At 404, the skin temperature is measured. At 406, it is determined whether the measured skin temperature is lower than a predetermined lower threshold. When the measured skin temperature is determined to be lower than the predetermined lower threshold, then at 408, the processor may cause the cold power relay to close and the warm power relay to open, thereby causing the skin temperature regulator to heat the skin. The regulation of the skin temperature by the skin temperature regulator may be performed during the emitting of light by the light source and the receiving of light by the photo-detector. At 410, it is determined whether the measured skin temperature is higher than a predetermined upper threshold. When the measured skin temperature is determined to be higher than the predetermined upper threshold, then at 412, the processor may cause the cold power relay to open and the warm power relay to close, thereby causing the skin temperature regulator to cool the skin. Alternatively, a cold power relay may not be opened, and the skin may be allowed to be cooled through passive heat dissipation. When it is determined that the measured skin temperature skin is within the desired temperature range, at which a desired SNR of the electrical output of the photo-detector is achieved that enables an identification of a target feature in an arterial pulse waveform of the illuminated arteries, or a detection of an absence of the target feature in the arterial pulse waveform of the illuminated arteries, at 414 the skin measurement process is performed by emitting light by the light source to illuminate arteries in subcutaneous tissue of the skin. At 416, the photo-detector receives the light illuminating the skin and generates an electrical output that is a function of the intensity of the received light. At 418, the processor generates, based on the electrical output, an output signal indicative of blood properties. This generation of electrical output may also be performed during the active regulation of the skin temperature by the skin temperature regulator. In one example, a diagnostic output may be generated based on the identification of the target feature, or the detection of the absence of the target feature. The target feature may be, but is not limited to, a dicrotic notch, an anacrotic notch, pulse peaks, pulse dips, pulse reflection points, slopes, slurring, pulse upstroke pattern, and pulse downstroke pattern. Following 418, at 420 the method returns to start again at 402.

In some embodiments, the methods and processes described herein may be tied to a computing system of one or more computing devices. In particular, such methods and processes may be implemented as a computer-application program or service, an application-programming interface (API), a library, and/or other computer-program product.

Figure 9:
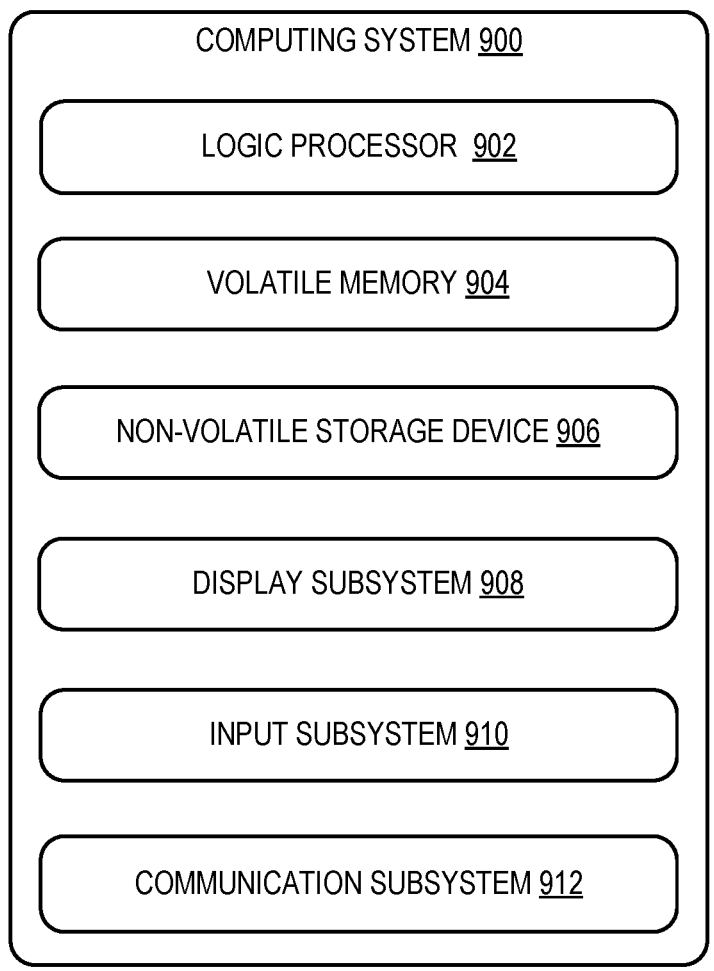
FIG. 9 shows an example computing environment that may be utilized in the embodiment of FIG. 1.

FIG. 9 schematically shows a non-limiting implementation of a computing system 900 that can enact one or more of the methods and processes described above. Computing system 900 is shown in simplified form. Computing system 900 may embody the photoplethysmogram device 10 of FIG. 1. Computing system 900 may take the form of one or more personal computers, server computers, tablet computers, home-entertainment computers, network computing devices, gaming devices, mobile computing devices, mobile communication devices (e.g., smart phone), and/or other computing devices, and wearable computing devices such as smart wristwatches and head mounted augmented reality devices.

Computing system 900 includes a logic processor 902 volatile memory 904, and a non-volatile storage device 906. Computing system 900 may optionally include a display subsystem 908, input subsystem 910, communication subsystem 912, and/or other components not shown in FIG. 9.

Logic processor 902 includes one or more physical devices configured to execute instructions. For example, the logic processor may be configured to execute instructions that are part of one or more applications, programs, routines, libraries, objects, components, data structures, or other logical constructs. Such instructions may be implemented to perform a task, implement a data type, transform the state of one or more components, achieve a technical effect, or otherwise arrive at a desired result.

The logic processor may include one or more physical processors (hardware) configured to execute software instructions. Additionally or alternatively, the logic processor may include one or more hardware logic circuits or firmware devices configured to execute hardware-implemented logic or firmware instructions. Processors of the logic processor 902 may be single-core or multi-core, and the instructions executed thereon may be configured for sequential, parallel, and/or distributed processing. Individual components of the logic processor optionally may be distributed among two or more separate devices, which may be remotely located and/or configured for coordinated processing. Aspects of the logic processor may be virtualized and executed by remotely accessible, networked computing devices configured in a cloud-computing configuration. In such a case, these virtualized aspects are run on different physical logic processors of various different machines, it will be understood.

Non-volatile storage device 906 includes one or more physical devices configured to hold instructions executable by the logic processors to implement the methods and processes described herein. When such methods and processes are implemented, the state of non-volatile storage device 906 may be transformed—e.g., to hold different data.

Non-volatile storage device 906 may include physical devices that are removable and/or built-in. Non-volatile storage device 906 may include optical memory (e.g., CD, DVD, HD-DVD, Blu-Ray Disc, etc.), semiconductor memory (e.g., ROM, EPROM, EEPROM, FLASH memory, etc.), and/or magnetic memory (e.g., hard-disk drive, floppy-disk drive, tape drive, MRAM, etc.), or other mass storage device technology. Non-volatile storage device 906 may include nonvolatile, dynamic, static, read/write, read-only, sequential-access, location-addressable, file-addressable, and/or content-addressable devices. It will be appreciated that non-volatile storage device 906 is configured to hold instructions even when power is cut to the non-volatile storage device 906.

Volatile memory 904 may include physical devices that include random access memory. Volatile memory 904 is typically utilized by logic processor 902 to temporarily store information during processing of software instructions. It will be appreciated that volatile memory 904 typically does not continue to store instructions when power is cut to the volatile memory 904.

Aspects of logic processor 902, volatile memory 904, and non-volatile storage device 906 may be integrated together into one or more hardware-logic components. Such hardware-logic components may include field-programmable gate arrays (FPGAs), program- and application-specific integrated circuits (PASIC/ASICs), program- and application-specific standard products (PSSP/ASSPs), system-on-a-chip (SOC), and complex programmable logic devices (CPLDs), for example.

The terms "module," "program," and "engine" may be used to describe an aspect of computing system 900 typically implemented in software by a processor to perform a particular function using portions of volatile memory, which function involves transformative processing that specially configures the processor to perform the function. Thus, a module, program, or engine may be instantiated via logic processor 902 executing instructions held by non-volatile storage device 906, using portions of volatile memory 904. It will be understood that different modules, programs, and/or engines may be instantiated from the same application, service, code block, object, library, routine, API, function, etc. Likewise, the same module, program, and/or engine may be instantiated by different applications, services, code blocks, objects, routines, APIs, functions, etc. The terms "module," "program," and "engine" may encompass individual or groups of executable files, data files, libraries, drivers, scripts, database records, etc.

When included, display subsystem 908 may be used to present a visual representation of data held by non-volatile storage device 906. The visual representation may take the form of a graphical user interface (GUI). As the herein described methods and processes change the data held by the non-volatile storage device, and thus transform the state of the non-volatile storage device, the state of display subsystem 908 may likewise be transformed to visually represent changes in the underlying data. Display subsystem 908 may include one or more display devices utilizing virtually any type of technology. Such display devices may be combined with logic processor 902, volatile memory 904, and/or non-volatile storage device 906 in a shared enclosure, or such display devices may be peripheral display devices.

When included, input subsystem 910 may comprise or interface with one or more user-input devices such as a keyboard, mouse, touch screen, or game controller. In some implementations, the input subsystem may comprise or interface with selected natural user input (NUI) componentry. Such componentry may be integrated or peripheral, and the transduction and/or processing of input actions may be handled on- or off-board. Example NUI componentry may include a microphone for speech and/or voice recognition; an infrared, color, stereoscopic, and/or depth camera for machine vision and/or gesture recognition; a head tracker, eye tracker, accelerometer, and/or gyroscope for motion detection and/or intent recognition; as well as electric-field sensing componentry for assessing brain activity; and/or any other suitable sensor.

When included, communication subsystem 912 may be configured to communicatively couple various computing devices described herein with each other, and with other devices. Communication subsystem 912 may include wired and/or wireless communication devices compatible with one or more different communication protocols. As non-limiting examples, the communication subsystem may be configured for communication via a wireless telephone network, or a wired or wireless local- or wide-area network, such as Bluetooth and HDMI over Wi-Fi connection. In some implementations, the communication subsystem may allow computing system 900 to send and/or receive messages to and/or from other devices via a network such as the Internet.

The following paragraphs provide additional support for the claims of the subject application. One aspect provides a photoplethysmogram device comprising a light source configured to emit light to illuminate skin; a photo-detector configured to receive the light illuminating the skin and generate an electrical output as a function of an intensity of the received light; a skin temperature regulator configured to regulate a temperature of the skin, the skin temperature regulator being a heating and/or cooling mechanism configured to heat and/or cool the skin; and a processor configured to generate, based on the electrical output, an output signal indicative of blood properties. In this aspect, additionally or alternatively, the skin temperature regulator may include a thermoelectric heat pump. In this aspect, additionally or alternatively, a copper plate may be attached to the thermoelectric heat pump to interface between the skin and the thermoelectric heat pump. In this aspect, additionally or alternatively, the skin temperature regulator may include a heating element. In this aspect, additionally or alternatively, the skin temperature regulator may be provided adjacent to the light source and the photo-detector. In this aspect, additionally or alternatively, the photoplethysmogram device may further comprise a thermometer configured to measure the temperature of the skin, the processor being configured to control the skin temperature regulator to heat or cool the skin toward a predetermined skin temperature based on the measured skin temperature. In this aspect, additionally or alternatively, the processor may be configured to generate the output signal indicative of blood properties after controlling the skin temperature regulator to heat or cool the skin to the predetermined skin temperature. In this aspect, additionally or alternatively, the processor may be configured to control the skin temperature regulator to heat or cool the skin to increase a signal-to-noise ratio (SNR) of the electrical output from the photo-detector at least 200%. In this aspect, additionally or alternatively, the light source, the photo-detector, and the skin temperature regulator may be housed in a wristband. In this aspect, additionally or alternatively, a user input device may be configured to receive a user input to control the skin temperature regulator.

Another aspect provides a photoplethysmography method comprising emitting light to illuminate skin of a user via a light source; receiving, via a photo-detector, the light illuminating the skin to generate an electrical output as a function of an intensity of the received light; regulating, via a heating and/or cooling mechanism configured to heat and/or cool the skin, a temperature of the skin adjacent to the light source and the photo-detector; and generating, based on the electrical output, an output signal indicative of blood properties. In this aspect, additionally or alternatively, the method may further comprise measuring the temperature of the skin; and controlling a power relay to regulate the temperature of the skin to heat or cool the skin toward a predetermined skin temperature based on the measured skin temperature. In this aspect, additionally or alternatively, the method may further comprise implementing a feedback loop to control the skin temperature within a predetermined skin temperature range that includes the predetermined skin temperature. In this aspect, additionally or alternatively, the method may further comprise regulating the temperature of the skin to heat or cool the skin to increase a SNR of the electrical output from the photo-detector at least 200%. In this aspect, additionally or alternatively, the temperature of the skin adjacent to the light source and the photo-detector may be regulated at a plurality of locations on the skin by a plurality of heating and/or cooling mechanisms. In this aspect, additionally or alternatively, the method may further comprise alternating between a heating period of heating the skin and a cooling period of cooling the skin; and evaluating changes in the electrical output generated by the photo-detector between the heating period and the cooling period. In this aspect, additionally or alternatively, the method may further comprise identifying a dicrotic notch in an arterial pulse waveform from the electrical output. In this aspect, additionally or alternatively, the method may further comprise responsive to a user operation of a push button, controlling the heating and/or cooling mechanism applied to the skin. In this aspect, additionally or alternatively, the method may further comprise adjusting the predetermined skin temperature based on a tone of the skin.

Another aspect provides a photoplethysmography method comprising emitting light to illuminate skin of a user via a light source; receiving, via a photo-detector, the light illuminating the skin to generate an electrical output as a function of an intensity of the received light; regulating, via a heating mechanism configured to heat the skin, a temperature of the skin adjacent to the light source and the photo-detector during the emitting and the receiving; and during the regulating, generating, based on the electrical output, an output signal indicative of blood properties, the heating mechanism being provided adjacent to the light source and the photo-detector in a photoplethysmogram device.

It will be understood that the configurations and/or approaches described herein are exemplary in nature, and that these specific embodiments or examples are not to be considered in a limiting sense, because numerous variations are possible. The specific routines or methods described herein may represent one or more of any number of processing strategies. As such, various acts illustrated and/or described may be performed in the sequence illustrated and/or described, in other sequences, in parallel, or omitted. Likewise, the order of the above-described processes may be changed.

The subject matter of the present disclosure includes all novel and non-obvious combinations and sub-combinations of the various processes, systems and configurations, and other features, functions, acts, and/or properties disclosed herein, as well as any and all equivalents thereof.

The invention claimed is:

1. A photoplethysmogram device comprising:
a light source configured to emit light to illuminate skin;
a photo-detector configured to receive the light illuminating the skin and generate an electrical output as a function of an intensity of the received light;
a skin temperature regulator configured to regulate a temperature of the skin, the skin temperature regulator being a heating and/or cooling mechanism configured to heat and/or cool the skin; and
a processor configured to:
control the skin temperature regulator to heat or cool the skin to increase a signal-to-noise ratio (SNR) of the electrical output from the photo-detector by a predetermined amount, and
generate, based on the electrical output, an output signal indicative of blood properties.

2. The device of claim 1, wherein
the skin temperature regulator includes a thermoelectric heat pump.

3. The device of claim 2, wherein
a copper plate is attached to the thermoelectric heat pump to interface between the skin and the thermoelectric heat pump.

4. The device of claim 1, wherein
the skin temperature regulator includes a heating element.

5. The device of claim 1, wherein
the skin temperature regulator is provided adjacent to the light source and the photo-detector.

6. The device of claim 1, further comprising:
a thermometer configured to measure the temperature of the skin, wherein
the processor is configured to control the skin temperature regulator to heat or cool the skin toward a predetermined skin temperature based on the measured skin temperature.

7. The device of claim 6, wherein
the processor is configured to generate the output signal indicative of blood properties after controlling the skin temperature regulator to heat or cool the skin to the predetermined skin temperature.

8. The device of claim 7, wherein
the light source, the photo-detector, and the skin temperature regulator are housed in a wristband.

9. The device of claim 1, further comprising:
a user input device configured to receive a user input to control the skin temperature regulator.

10. The photoplethysmogram device of claim 1, wherein the light source and photo-detector are each located closer to a skin-interfacing surface of the device that interfaces with the skin as compared to the heating and/or cooling mechanism.

11. The photoplethysmogram device of claim 1, further comprising a heat conductive plate located between a skin-interfacing surface and the heating and/or cooling mechanism.

12. A photoplethysmography method comprising:
emitting light to illuminate skin of a user via a light source;
receiving, via a photo-detector, the light illuminating the skin to generate an electrical output as a function of an intensity of the received light;
regulating, via a heating and/or cooling mechanism configured to heat and/or cool the skin, a temperature of the skin adjacent to the light source and the photo-detector to increase a signal-to-noise ratio (SNR) of the electrical output from the photo-detector by a predetermined amount; and
generating, based on the electrical output, an output signal indicative of blood properties.

13. The method of claim 12, further comprising:
measuring the temperature of the skin; and controlling a power relay to regulate the temperature of the skin to heat or cool the skin toward a predetermined skin temperature based on the measured skin temperature.

14. The method of claim 13, further comprising:
implementing a feedback loop to control the skin temperature within a predetermined skin temperature range that includes the predetermined skin temperature.

15. The method of claim 13, further comprising:
adjusting the predetermined skin temperature based on a tone of the skin.

16. The method of claim 12, wherein
the temperature of the skin adjacent to the light source and the photo-detector is regulated at a plurality of locations on the skin by a plurality of heating and/or cooling mechanisms.

17. The method of claim 12, further comprising:
alternating between a heating period of heating the skin and a cooling period of cooling the skin; and
evaluating changes in the electrical output generated by the photo-detector between the heating period and the cooling period.

18. The method of claim 12, further comprising:
identifying a dicrotic notch in an arterial pulse waveform from the electrical output.

19. The method of claim 12, further comprising:
responsive to a user operation of a push button, controlling the heating and/or cooling mechanism applied to the skin.

20. A photoplethysmogram device comprising:
a light source configured to emit light to illuminate skin;
a photo-detector configured to receive the light illuminating the skin and generate an electrical output as a function of an intensity of the received light;
a skin temperature regulator configured to regulate a temperature of the skin, the skin temperature regulator being a heating and/or cooling mechanism configured to heat and/or cool the skin;
a processor configured to generate, based on the electrical output, an output signal indicative of blood properties; and
a heat conductive plate located between a skin-interfacing surface and the heating and/or cooling mechanism,
wherein the light source, the photo-detector, and the heat conductive plate are each located closer to the skin-interfacing surface of the device that interfaces with the skin as compared to the heating and/or cooling mechanism.

* * * * *